United States Patent
Khazzam et al.

[11] Patent Number: 5,906,489
[45] Date of Patent: May 25, 1999

[54] TEMPORARY DENTAL IMPLANT

[75] Inventors: Joseph N. Khazzam, Oyster Bay Cove; Babak Ghalili, New York, both of N.Y.

[73] Assignee: Biotech Medical Instruments Corp., Hauppauge, N.Y.

[21] Appl. No.: 09/095,343

[22] Filed: Jun. 10, 1998

[51] Int. Cl.⁶ .................................................. A61C 8/00
[52] U.S. Cl. ........................ 433/176; 433/173; 433/174
[58] Field of Search .................................... 433/172, 173, 433/174, 175, 176

[56] References Cited

U.S. PATENT DOCUMENTS

| | | | |
|---|---|---|---|
| 4,702,697 | 10/1987 | Linkow | 433/173 |
| 4,964,801 | 10/1990 | Kawahara et al. | 433/173 |
| 5,052,930 | 10/1991 | Lodde et al. | 433/173 |

FOREIGN PATENT DOCUMENTS 2237598  2/1974  Germany ................................ 433/176

Primary Examiner—John J. Wilson
Attorney, Agent, or Firm—Darby & Darby

[57] ABSTRACT

An implant for supporting a prosthesis includes a base sheet that has a longitudinal axis and a lateral axis. At least two holes extend through the base sheet. A post is connected to the base sheet. The temporary dental implant is installed over a patient's jaw bone by exposing the jaw bone by displacing covering tissue. The base sheet is shaped into a U-shape so that the legs of the U-shape are directed away from the post. The shaped base sheet is installed over the jaw bone by securing the covering tissue to the jaw bone and loading a prosthesis onto the post.

31 Claims, 5 Drawing Sheets

TEMPORARY DENTAL IMPLANT

BACKGROUND OF THE INVENTION

1. Field of the Invention

This invention relates to dental implants and, more particularly, to a structure and a method for supporting temporary protheses.

2. Discussion of the Related Art

When a tooth or teeth are missing, the installation of an implant into a human jaw bone is quite common to replace the missing tooth for chewing and/or cosmetic reasons. The implant is typically a metal "fixture" inserted into the jaw bone, where the missing tooth or teeth are, to form a substitute "root" upon which a prosthesis is "loaded" or installed over the fixture, to replace natural teeth. This procedure can be done for a single tooth as well as a whole jaw bone of missing teeth.

A problem with such implants is that the fixture must remain submerged into the bone for a long period of time, typically from four to six months, to allow the fixture to ossio-integrate and become solidly held by the surrounding bone before a prosthesis can be loaded upon the fixture. Thus, during these four to six months, which is the required period for ossio-integration, the patient is essentially toothless.

To overcome this problem, one publication installs a temporary prosthesis with a butterfly system on the lingual side, or the side facing the tongue and adheres the butterflies to the adjacent teeth. Another publication uses a removable bridge instead of the butterfly system to hold the temporary prosthesis in place by also utilizing the adjacent teeth for anchoring. Although these publications have solved the toothless problem during the ossio-integration period by providing the patient with a temporary prosthesis for chewing and cosmetic reasons, these publications also have several disadvantages.

One disadvantage is that the temporary prosthesis has relatively weak stability because the butterfly system or the removable bridge adheres to adjacent teeth for stability. Another disadvantage is that the adjacent teeth are easily damaged by the additional external forces such as chewing that are applied by the temporary prosthesis. Another disadvantage is that the adjacent teeth can be damaged when the dentist removes the temporary prosthesis.

SUMMARY OF THE INVENTION

The present invention is a temporary dental implant that has holes in its buccal/lingual legs as described and discussed below to enable the dentist to load the temporary prosthesis upon it without using the adjacent teeth for anchoring because these holes allow the gingivae to grow through these holes and re-attach to the jaw bone (typically within three to four days) and, thus, holding the temporary dental implant in accordance with the present invention in place.

Thus, it is an object of the present invention to provide a structure and method for supporting a temporary prosthesis with great stability, without relying on the adjacent teeth for stability, and, thus, without damaging the adjacent teeth.

In accordance with a preferred embodiment of the present invention, the temporary dental implant includes an implant for supporting a prosthesis includes a base sheet that has a longitudinal axis and a lateral axis. At least two holes extend through the base sheet. A post is connected to the base sheet. The temporary dental implant is installed over a patient's jaw bone by exposing the jaw bone by displacing covering tissue. The base sheet is shaped into a U-shape so that the legs of the U-shape are directed away from the post. The shaped base sheet is installed over the jaw bone by securing the covering tissue to the jaw bone and loading a prosthesis onto the post.

BRIEF DESCRIPTION OF THE DRAWINGS

The above and still further objects, features and advantages of the present invention will become apparent upon consideration of the following detailed description of a specific embodiment thereof, especially when taken in conjunction with the accompanying drawings wherein.

DETAILED DESCRIPTION OF THE PREFERRED EMBODIMENTS

Figure 1:
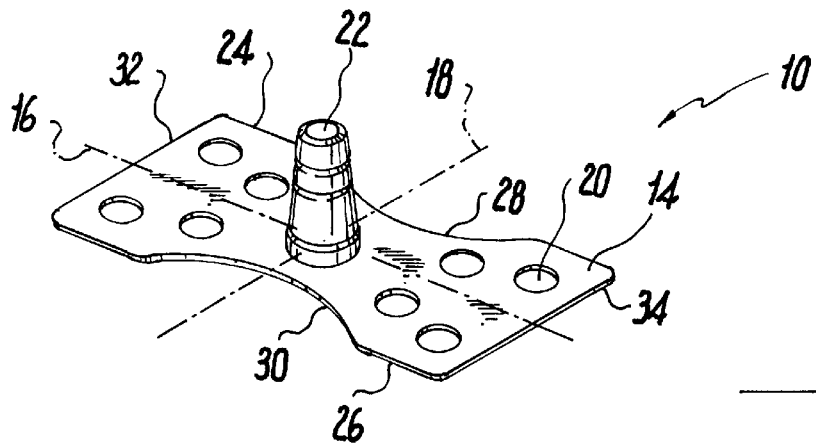
FIG. 1 is a perspective view of a first preferred embodiment of a temporary dental implant, which supports a temporary prosthesis, according to the present invention.

Referring now to FIGS. 1–4, and in accordance with a first embodiment of the present invention, a temporary dental implant (structure) 10 for supporting a prosthesis 12 is illustrated. Supporting is defined to mean that the temporary dental implant 10 provides a prosthetic abutment 22 to hold the prosthesis 12 in place, i.e., the prosthesis 12 is "loaded" onto the prosthetic abutment 22 as described and illustrated in FIGS. 2 and 3.

The temporary dental implant 10 includes a base sheet 14 having a longitudinal axis 16 and a lateral axis 18. A prosthetic abutment 22 is connected to base sheet 14, preferably at the intersection between the longitudinal axis 16 and the lateral axis 18. Base sheet 14 has at least one hole 20, and preferably a plurality of holes, extending through it on each side of the lateral axis 18. Holes 20 are preferably substantially circular. The first exemplary embodiment has four holes 20 disposed on each side of lateral axis 18. Furthermore, base sheet 14 is enclosed by a first edge 24, a second edge 26, a third edge 32, and a fourth edge 34. The first edge 24 has a first intermediate recessed portion 28, which preferably is concaved toward the prosthetic abutment 22. Similarly, the second edge 26 has a second intermediate recessed portion 30, which also preferably is concaved toward the prosthetic abutment 22. The third edge 32 and the fourth edge 34 are preferably substantially straight.

Figure 2:
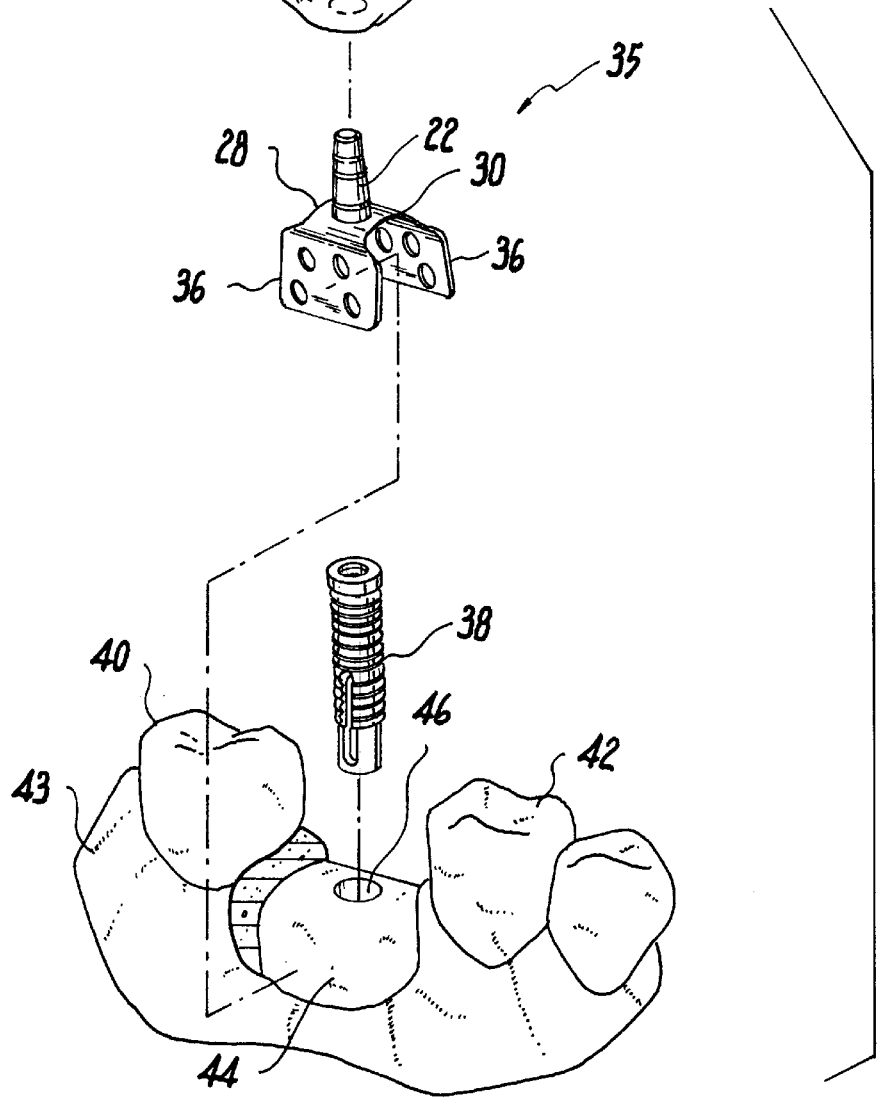
FIG. 2 is an exploded view of a first preferred method of installing the first preferred embodiment, which has been bent to tightly cap the jaw bone.
Figure 3:
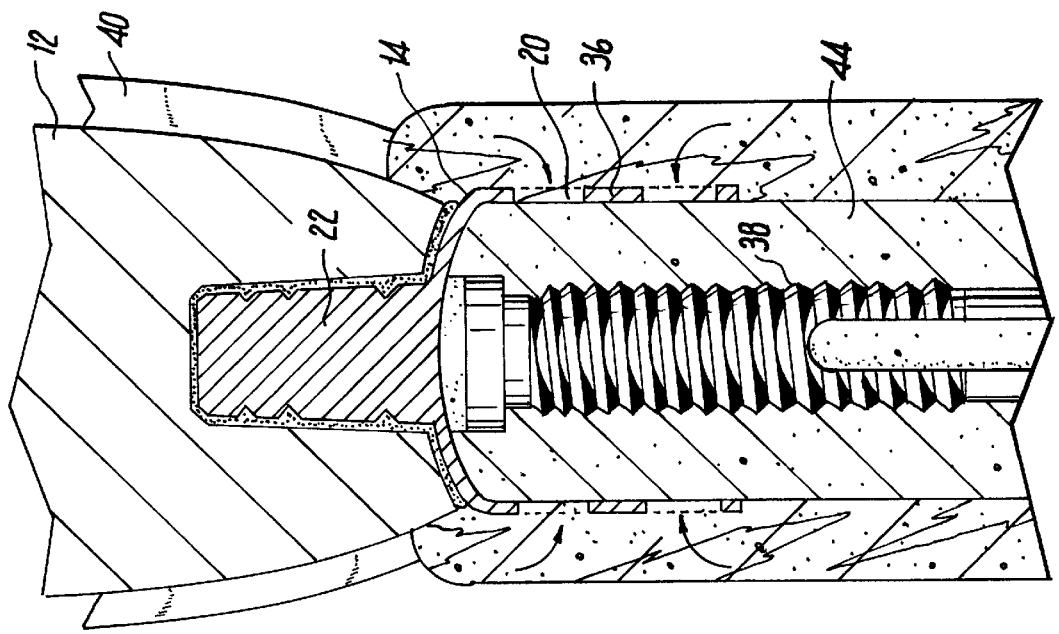
FIG. 3 is a side view of the first preferred embodiment with its prosthetic abutment positioning substantially, directly above the permanent dental implant.

Referring now to FIG. 2, when installing the first embodiment of the temporary dental implant 10 over a patient's jaw bone 44 where a tooth is missing, the dentist first would expose the jaw bone 44 by removing gingivae (gum tissues) 43. Second, the dentist would drill an opening 46 in the jaw bone 44. Third, the dentist would insert a permanent dental implant 38 into the opening 46. These first three steps are conventional and are well known to those skilled in the art.

Fourth, the dentist shapes the base sheet 14 of the temporary dental implant 10 in a direction away from the prosthetic abutment 22 to form a custom, U-shape temporary dental implant 35. The custom, U-shape temporary dental implant 35 is then fitted over the jaw bone 44 so that the prosthetic abutment 22 is substantially coaxial with the permanent dental implant 38 and the now U-shaped base sheet comfortably, but tightly fits over the jaw bone. The custom, U-shape temporary dental implant 35 has two buccal/lingual legs 36 that are formed when the dentist shapes the base sheet 14. For this fourth step, the dentist either could shape the temporary dental implant 10 before the implantation without the presence of the patient or could shape the temporary dental implant 10 during the implantation. If the dentist chooses to shape the temporary dental implant 10 before the implantation, sufficient x-rays of the jaw bone 44 must be taken to ensure that the dentist would have adequate knowledge of the shape of the jaw bone 44. If the dentist chooses to shape the temporary dental implant 10 during the implantation, referring to FIG. 3, the dentist first could place the temporary dental implant 10 over and coaxially align the prosthetic abutment 22, which is extending away from the jaw bone 44, with the permanent dental implant 38, which has been embedded within the jaw bone 44. The dentist then would mark the base sheet 14 of the temporary dental implant 10 at 49, where the base sheet 14 touches the jaw bone 44. Next, the dentist would bend the base sheet 14 in a direction away from the prosthetic abutment 22 about location 49 and form the custom, U-shape temporary dental implant 35 so that the custom, U-shape temporary dental implant 35 will comfortably, but tightly, saddle over the jaw bone 44. Of course, as the dentist becomes more familiar with the process, he or she could bend the base sheet based on a visual inspection of the jaw bone.

Figure 4:
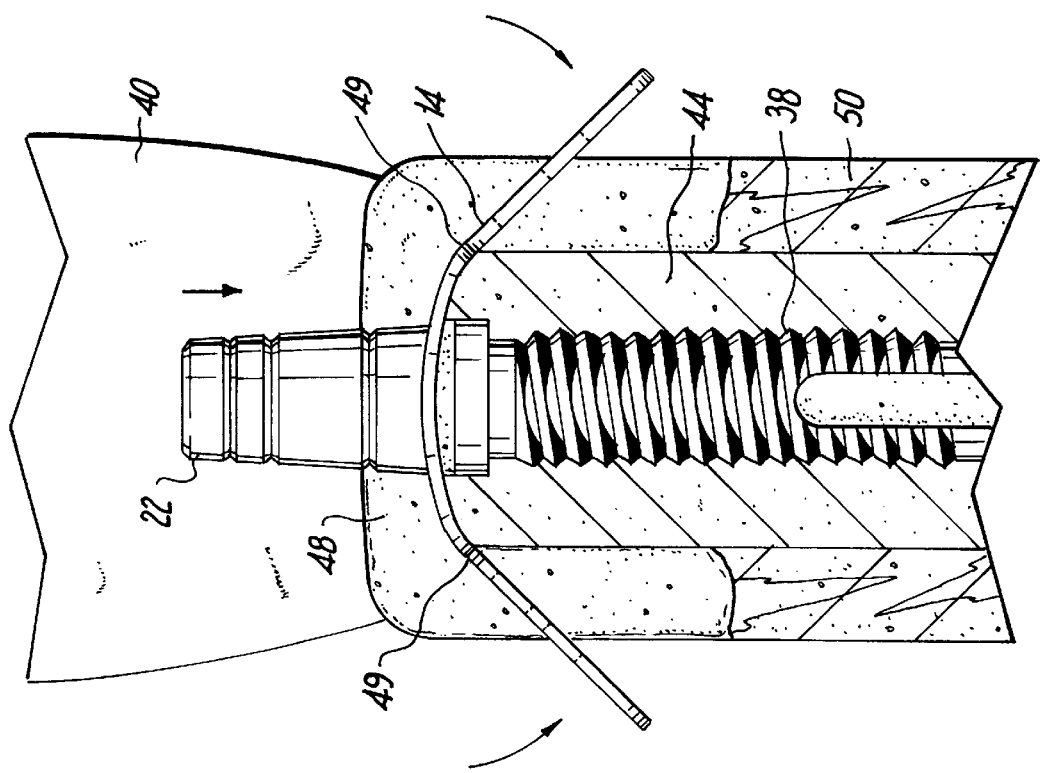
FIG. 4 is a cross-sectional view of the first preferred embodiment tightly installed between the jaw bone and the gingivae, and the temporary prosthesis loaded over the prosthetic abutment.

Fifth, referring to FIGS. 2 and 4, the dentist would install the custom, U-shape temporary dental implant 35 over the jaw bone 44 with the prosthetic abutment 22 directly above the permanent dental implant 38. The dentist would next suture the gingivae 43 back in position, also in any conventional manner. Finally, the dentist loads the prosthesis 12 onto the prosthetic abutment 22 in any conventional manner. The dentist preferably loads prosthesis 12 only about three to four days after the temporary dental implant 10 has been installed, thereby allowing implant 10 to be securely anchored before the prosthesis is used for chewing.

As described and illustrated in FIGS. 1–4, the first and second intermediate recessed portions, 28 and 30 respectively, are sufficiently, inwardly concaved toward the prosthetic abutment 22 to accommodate first and second adjacent teeth, 40 and 42 respectively, by not contacting with and, thus, preventing any abrasion against the first and second adjacent teeth, 40 and 42 respectively. Moreover, the holes 20 of the buccal/lingual legs 36 are essential to the present invention because they allow the gingivae surrounding the missing tooth 50 to grow through the holes, thereby reattaching themselves to the jaw bone 44. This growth of the gingivae typically takes place in three to four days, and assists in holding the temporary dental implant 10 securely against and on top of the jaw bone 44. Therefore, depending upon the area and structural integrity of the base sheet 14, having more holes 20 preferably extending through the buccal/lingual legs 36 provides better stability for the temporary dental implant 10 after installation. Furthermore, the holes 20 are preferably located on the buccal/lingual legs 36 such that upon installation, the holes 20 lie between the gingivae 43 and the jaw bone 44.

Referring now to FIGS. 5–8, and in accordance with a second embodiment of the present invention, a temporary dental implant (structure) 11 for supporting the prosthesis 12 is illustrated. The embodiments of FIGS. 5–8 differs from the embodiment shown in FIGS. 1–4 in the shape of base sheet 14. The base sheet 14 has at least one hole 52 disposed on each side of the lateral axis 18. Holes 52 are substantially oval. Furthermore, the base sheet 14 is enclosed by substantially straight edges 54, a first intermediate recessed portion 56, and a second intermediate recessed portion 58. The first and second intermediate recessed portions 56 and 58, respectively are preferably concave. Substantially straight edges 54 merge with the first intermediate recessed portion 56 to form a first corner. Another two substantially straight edges 54 also merge with the second intermediate recessed portion 58 to form a second corner. Then two more substantially straight edges 54 merge with the first corner to form two ninety degrees angles 60, which open away from the prosthetic abutment 22. Similarly, another two substantially straight edges 54 merge with the second corner to form two more ninety degrees angles 61, which also open away from the prosthetic abutment 22. Furthermore, two additional substantially straight edges 54 continue to merge with the substantially straight edges 54, which have formed the ninety degrees angles 60 with the first corner, to form two obtuse angles 62 that open toward the prosthetic abutment 22. Likewise, two more substantially straight edges 54 also continue to merge with the substantially straight edges 54, which have formed the ninety degrees angles 61 with the second corner, to form two obtuse angles 63 that similarly open toward the prosthetic abutment 22.

Figure 5:
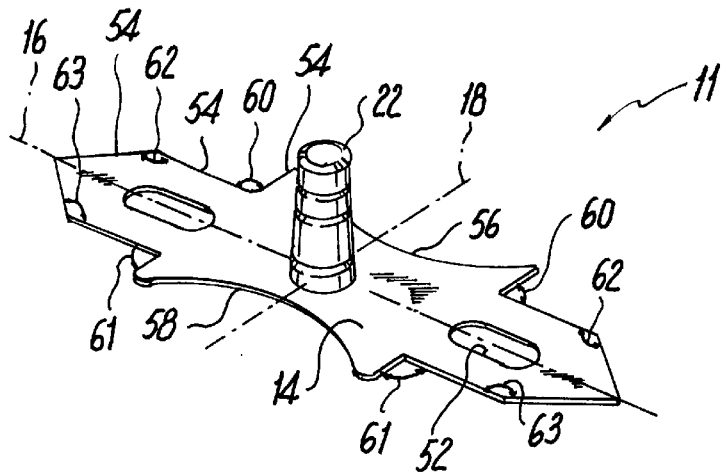
FIG. 5 is a perspective view of a second preferred embodiment, which supports the temporary prothesis, according to the present invention.
Figure 6:
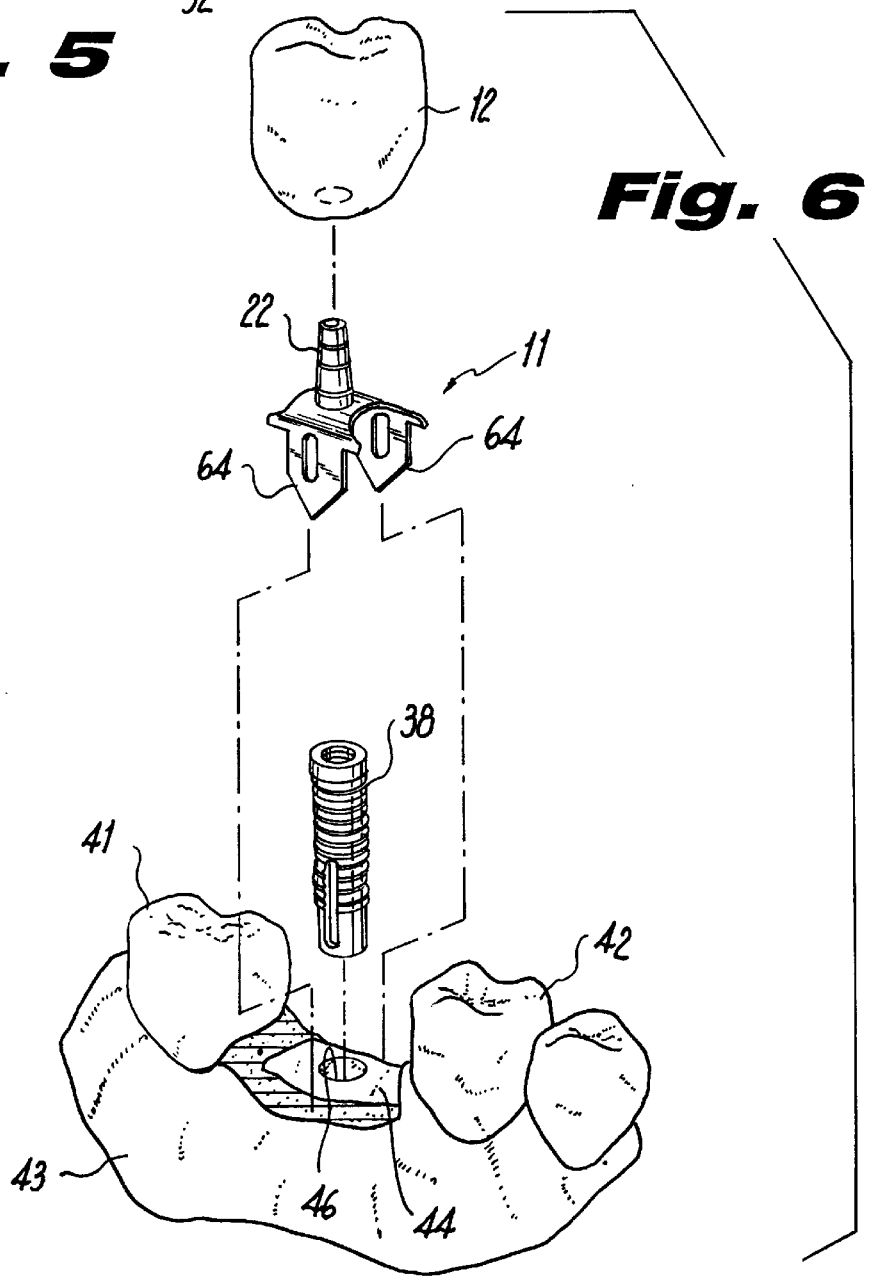
FIG. 6 is an exploded view of a first preferred method of installing the second preferred embodiment, which has been bent to tightly cap the jaw bone.
Figure 7:
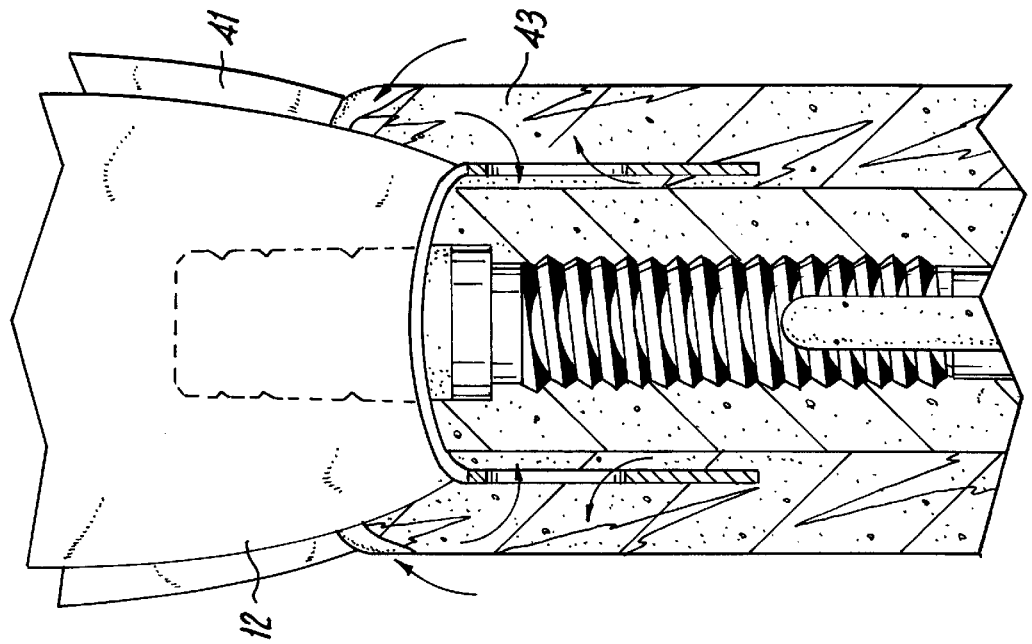
FIG. 7 is a side view of the second preferred embodiment with its prosthesis abutment positioning substantially, directly above the permanent dental implant.
Figure 8:
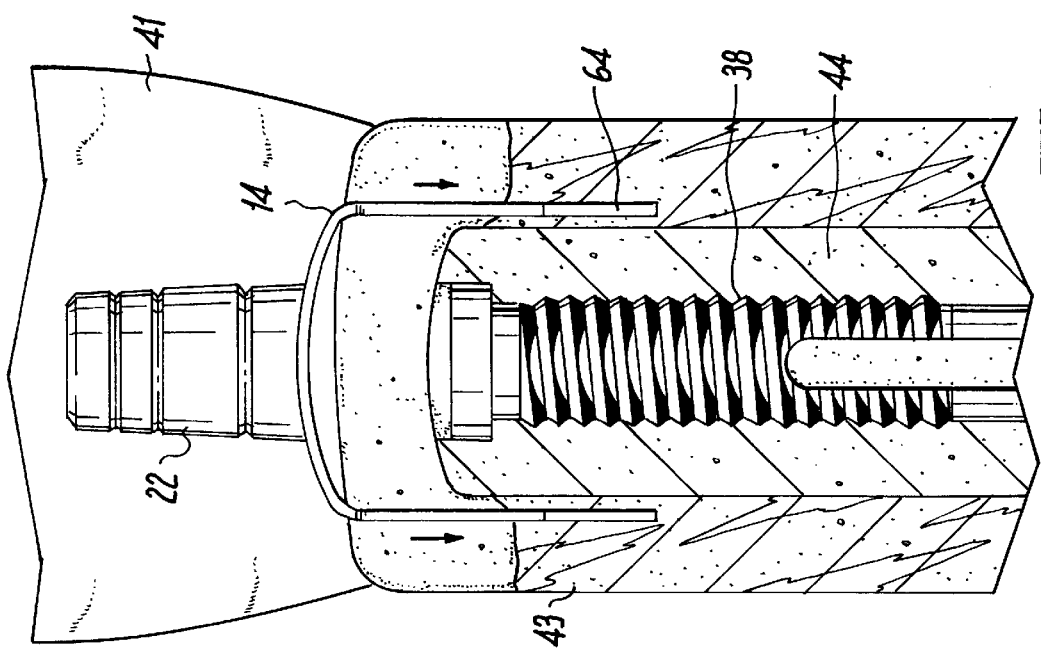
FIG. 8 is a cross-sectional view of the second preferred embodiment tightly installed between the jaw bone and the gingivae, and the temporary prosthesis loaded over the prosthesis abutment.

Referring to FIGS. 6–8, when installing the second embodiment of the temporary dental implant 11 over a patient's jaw bone 44 where a tooth is missing, the procedures are substantially the same as the procedures described above for the installation of the first embodiment of the present invention. However, the shape of buccal/lingual legs 64, as illustrated by FIG. 5 is designed to facilitate easier installation of temporary dental implant 11 by enabling legs 64 to be inserted through the gingivae 43 without exposing the underlying jaw bone 44 by removing the gingivae 43, and, thus, eliminating or minimizing the suturing of the gingivae 43 back in position.

As illustrated in FIGS. 5–8, the first and second intermediate recessed portions 56 and 58, respectively, are sufficiently concaved to accommodate first and second adjacent teeth 41 and 42, respectively, by not contacting with and, thus, preventing any abrasion against the first and second adjacent teeth, 41 and 42, respectively. Moreover, the holes 52 of the buccal/lingual legs 64 or base sheet 14 are important to the present invention because they allow the gingivae in and around the area of the missing tooth 50 to grow and reattach to the jaw bone 44, typically in three to four days. Thus, the temporary dental implant 11 is securely held against and on top of the jaw bone 44. Therefore, depending upon the area and structural integrity of the base sheet 14, having more holes 52 preferably extending through the buccal/lingual legs 64 provides better stability for the temporary dental implant 11 after installation. Furthermore, the holes 52 are preferably located on the buccal/lingual legs 64 such that upon installation, the holes 52 lie between the gingivae 43 and the jaw bone 44.

Figure 9:
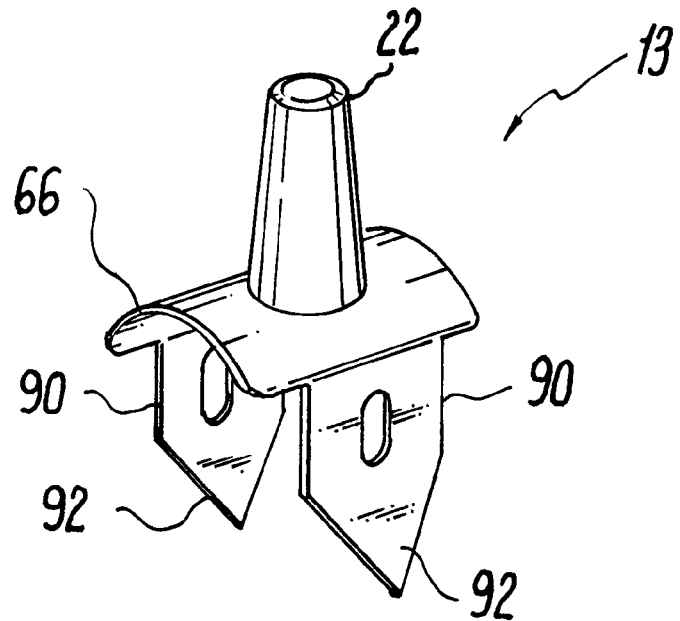
FIG. 9 is a perspective view of a third preferred embodiment, which supports the temporary prothesis, according to the present invention.

Referring to FIG. 9, and in accordance with a third embodiment of the present invention, a temporary dental implant (structure) 13 for supporting the prosthesis 12 is illustrated. The third embodiment is essentially the same as the second embodiment as illustrated in FIGS. 5–8 in all respects with the exception of its intermediate protruding portions 66, which are outwardly concave, not inwardly concave. Additionally, each leg 90 terminates in a v-shaped wedge 92. Wedges 92 are shaped to permit implant 13 to be fitted over the jaw bone without requiring the gingivae to be peeled away from the jaw bone. The approximate dimensions of this third embodiment may, as a non-limiting example, be as follows:

prosthetic abutment height=4.5–5.0 mm
coronal width of an intermediate protruding portion (longitudinally)=5.5–6.0 mm
length of buccal/lingual legs: including shaped intermediate protruding portion=5.0 mm
apical width of buccal/lingual legs=2.0 mm
I.D. between buccal/lingual legs=3.0 mm The method for installing the third embodiment of the present invention is the same as the method described above for installing the second embodiment.

Figure 10:
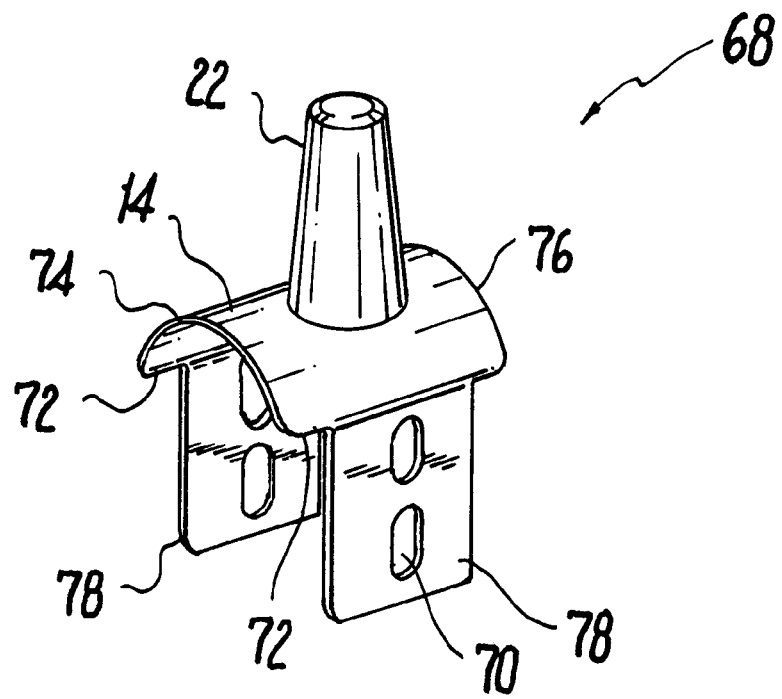
FIG. 10 is a perspective view of a fourth preferred embodiment, which supports the temporary prothesis, according to the present invention.

Referring to FIG. 10, and in accordance with a fourth embodiment of the present invention, a temporary dental implant (structure) 68 for supporting a prosthesis 12 is illustrated.

In the fourth embodiment of FIG. 10, the temporary dental implant 68 includes a base sheet 14 to which the prosthetic abutment 22 is connected, preferably at the intersection between a longitudinal axis 16 and a lateral axis 18 of the temporary dental implant 68. The holes 70 are substantially circular. This fourth embodiment preferably has two holes 70 on each side of the lateral axis 18. Furthermore, the base sheet 14 is enclosed by substantially straight edges 72, a first intermediate protruding portion 74, which preferably is concaved away from the prosthetic abutment 22, and a second intermediate protruding portion 76, which also preferably is concaved away from the prosthetic abutment 22. The two substantially straight edges 72 merge with the first intermediate protruding portion 74 to form a first corner. Another two substantially straight edges 72 also merge with the second intermediate protruding portion 76 to form a second corner. Then two more substantially straight edges 72 merge with the first corner to form two ninety degrees angles 80, which open away from the prosthetic abutment 22. Similarly, another two substantially straight edges 72 merge with the second corner to form two more ninety degrees angles 82, which also open away from the prosthetic abutment 22. Furthermore, two additional substantially straight edges 72 continue to merge with the substantially straight edges 72, which have formed the ninety degrees angles 80 with the first corner, to form two other ninety degrees angles 84 that open toward the prosthetic abutment 22. Likewise, two more substantially straight edges 72 also continue to merge with the substantially straight edges 72, which have formed the ninety degrees angles 82 with the second corner, to form two other ninety degrees angles 86 that similarly open toward the prosthetic abutment 22.

As illustrated in FIG. 10, the first and second intermediate protruding portions 74 and 76, respectively, are sufficiently, outwardly concaved away from the prosthetic abutment 22 to accommodate adjacent teeth, by not contacting with and thus preventing any abrasion against the adjacent teeth. Moreover, the holes 70 of the buccal/lingual legs 78 are important to the present invention because they allow the gingivae to grow and reattach to the jaw bone, typically in three to four days. Thus, the temporary dental implant 68 is securely held against and on top of the jaw bone. Therefore, depending upon the area and structural integrity of the base sheet 14, having more holes 70 preferably extending through the buccal/lingual legs 78 means better stability for the temporary dental implant 68 after installation. Furthermore, the holes 70 are preferably located on the buccal/lingual legs 78 such that when installing, the holes 70 would lie between the gingivae and the jaw bone.

The method for installing the fourth embodiment of the present invention is the same as the method described above for installing the first or second embodiment.

Each embodiment of the present invention could have more than one prosthetic abutment attached to the base sheet to accommodate a jaw with more than one missing tooth.

We claim:

1. An implant for supporting a prosthesis comprising:
    a base sheet capable of being formed around a patient's jaw bone, said base sheet having at least two holes extending therethrough, a longitudinal axis, a lateral axis, a first edge on a first side of said longitudinal axis, and a second edge on an opposing second side of said longitudinal axis, said first edge having a first intermediate recessed portion to accommodate a first adjacent tooth when said base sheet is positioned over said jaw bone, and said second edge having a second intermediate recessed portion to accommodate a second adjacent tooth when said base sheet is positioned over said jaw bone; and
    a post connected to said base sheet.

2. The implant as claimed in claim 1, wherein said post is connected to said base sheet substantially at an intersection between said longitudinal axis and said lateral axis.

3. The implant as claimed in claim 1, wherein at least one of said holes is located on a first side of said lateral axis and at least one of said holes is located on an opposing second side of said lateral axis.

4. The implant as claimed in claim 1, wherein said holes are substantially circular.

5. The implant as claimed in claim 1, wherein said base sheet, which is capable of being formed around a patient's jaw bone, has a third edge on a third side of said lateral axis and a fourth edge on an opposing fourth side of said lateral axis, said third edge is substantially straight, and said fourth edge is substantially straight.

6. The implant as claimed in claim 1, wherein said first intermediate recessed portion is inwardly concave toward said post.

7. The implant as claimed in claim 1, wherein said second intermediate recessed portion is inwardly concave toward said post.

8. The implant as claimed in claim 1, wherein said holes are substantially oval.

9. An implant for supporting a prosthesis comprising:
a base sheet capable of being formed around a patient's jaw bone, said base sheet having at least two holes extending therethrough, a longitudinal axis, a lateral axis, at least two substantially straight edges on a first side on a first side of said longitudinal axis and on an opposing second side of said longitudinal axis, a first intermediate recessed portion on said first side of said longitudinal axis to accommodate a first adjacent tooth when said base sheet is positioned over said jaw bone, and a second intermediate recessed portion on said second side of said longitudinal axis to accommodate a second adjacent tooth when said base sheet is positioned over said jaw bone; and
a post connected to said base sheet.

10. The implant as claimed in claim 9, wherein two of said substantially straight edges each merge with said first intermediate recessed portion on said first side of said longitudinal axis.

11. The implant as claimed in claim 10, wherein said merger substantially forms two ninety degrees angles, which open away from said post, with two said substantially straight edges.

12. The implant as claimed in claim 11, wherein said merger substantially forms two obtuse angles, which open toward said post.

13. The implant as claimed in claim 9, wherein two of said substantially straight edges each merge with said second intermediate recessed portion on said second side of said longitudinal axis.

14. The implant as claimed in claim 13, wherein said merger substantially forms two ninety degrees angles, which open away from said post, with two said substantially straight edges.

15. The implant as claimed in claim 14, wherein said merger substantially forms two obtuse angles, which open toward said post.

16. An implant for supporting a prosthesis comprising:
a base sheet capable of being formed around a patient's jaw bone, said base sheet having at least two substantially oval holes extending therethrough, a longitudinal axis, a lateral axis, at least two substantially straight edges on a first side on a first side of said longitudinal axis and on an opposing second side of said longitudinal axis, a first intermediate protruding portion on said first side of said longitudinal axis, and a second intermediate protruding portion on said second side of said longitudinal axis, two of said substantially straight edges each merge with said first intermediate protruding portion on said first side of said longitudinal axis; and
a post connected to said base sheet.

17. The implant as claimed in claim 16, wherein two of said substantially straight edges each merge with said second intermediate protruding portion on said second side of said longitudinal axis.

18. The implant as claimed in claim 17, wherein said merger substantially forms two ninety degrees angles, which open away from said post, with two said substantially straight edges.

19. The implant as claimed in claim 18, wherein said merger substantially forms two ninety degrees angles, which open away from said post, with two said substantially straight edges.

20. The implant as claimed in claim 19, wherein said merger substantially forms two obtuse angles, which open toward said post.

21. The implant as claimed in claim 20, wherein said merger substantially forms two obtuse angles, which open toward said post.

22. An implant for supporting a prosthesis comprising:
a base sheet capable of being formed around a patient's jaw bone, said base sheet having at least two substantially circular holes extending therethrough, a longitudinal axis, a lateral axis, at least two substantially straight edges on a first side of said longitudinal axis and on an opposing second side of said longitudinal axis, a first intermediate protruding portion on said first side of said longitudinal axis, and a second intermediate protruding portion on said second side of said longitudinal axis, two of said substantially straight edges each merge with said first intermediate protruding portion on said first side of said longitudinal axis; and
a post connected to said base sheet.

23. The implant as claimed in claim 22, wherein two of said substantially straight edges each merge with said second intermediate protruding portion on said second side of said longitudinal axis.

24. The implant as claimed in claim 23, wherein said merger substantially forms two ninety degrees angles, which open away from said post, with two said substantially straight edges.

25. The implant as claimed in claim 24, wherein said merger substantially forms two ninety degrees angles, which open away from said post, with two said substantially straight edges.

26. The implant as claimed in claim 25, wherein said merger substantially forms two ninety degrees angles, which open toward said post.

27. The implant as claimed in claim 26, wherein said merger substantially forms two ninety degrees angles, which open toward said post.

28. A method for installing a temporary dental implant, which includes a base sheet and a post, over a patient's jaw bone comprising the steps of:
exposing said jaw bone by displacing covering tissues;
positioning said temporary dental implant over said jaw bone and a permanent dental implant such that said post is protruding away from said jaw bone and is substantially coaxial with respect to said permanent dental implant;
shaping said base sheet in a direction away from said post to form a custom, substantially U-shape temporary dental implant;
installing said temporary dental implant over said jaw bone;
securing said covering tissue to said jaw bone; and
loading a prosthesis onto said post.

29. The method as claimed in claim 28, wherein, between said steps of exposing and positioning, further comprising the steps of:
forming an opening in said jaw bone; and
installing said permanent dental implant in said opening.

30. A method for installing a temporary dental implant, which includes a base sheet and a post, over a patient's jaw bone comprising the steps of:
shaping said base sheet in a direction away from said post to form a custom, substantially U-shape temporary dental implant;
forming an opening in said jaw bone;
installing a permanent dental implant in said opening;

installing said temporary dental implant over said jaw bone and permanent dental implant, and under covering tissues; and loading a prosthesis onto said post.

31. A method for installing a temporary dental implant, which includes a base sheet and a post, over a patient's jaw bone, where a tooth is missing, comprising the steps of:

forming an opening in said jaw bone;

installing a permanent dental implant in said opening;

positioning said temporary dental implant over said jaw bone and said permanent dental implant such that said post is protruding away from said jaw bone and substantially coaxial with respect to said permanent dental implant;

shaping said base sheet in a direction away from said post to form a custom, substantially U-shape temporary dental implant;

installing said temporary dental implant over said jaw bone;

loading a prosthesis onto said post.

* * * * *